CHRYSANTHEMUM PLANT
Filed Oct. 16, 1973 2 Sheets-Sheet 1
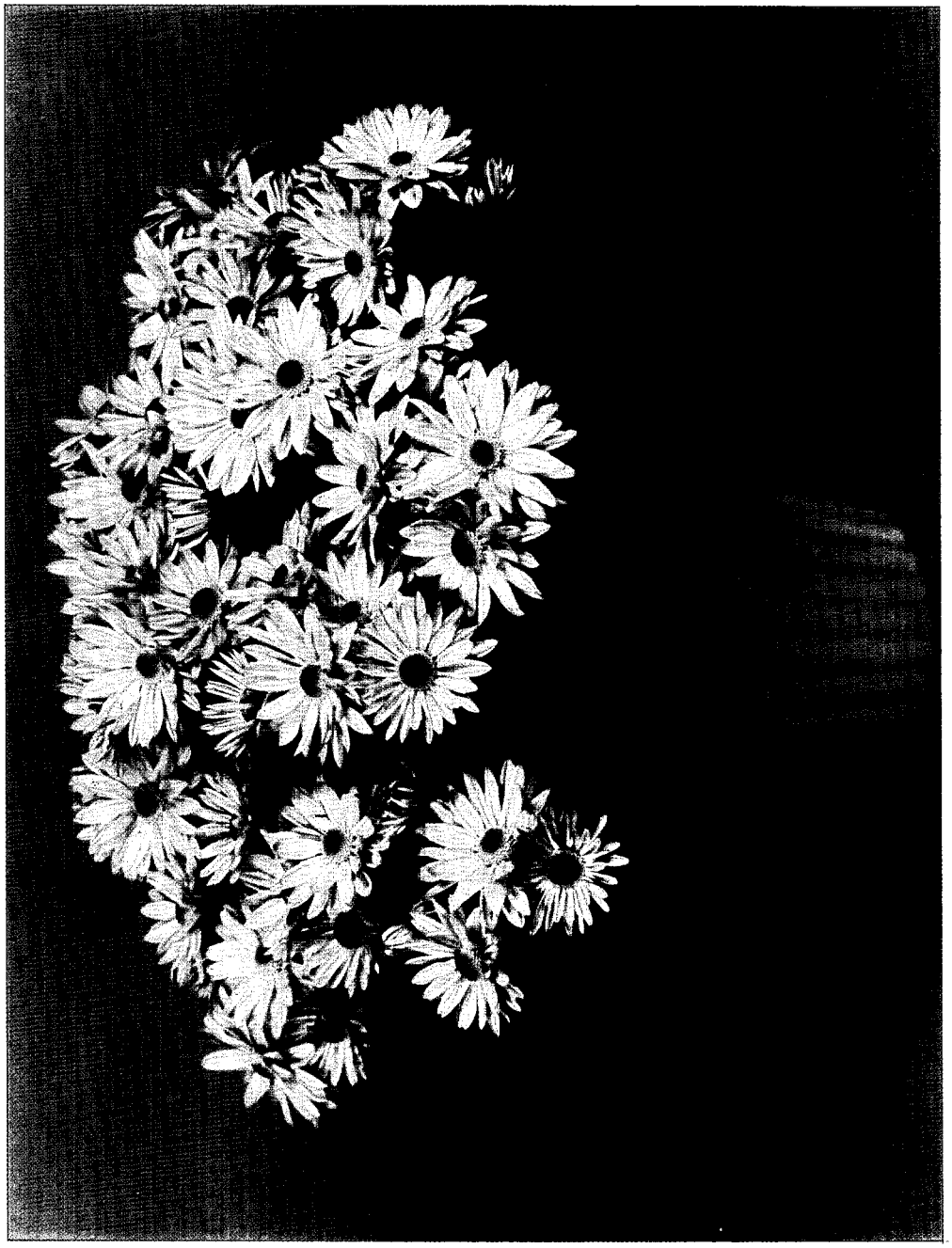

CHRYSANTHEMUM PLANT
Filed Oct. 16, 1973 2 Sheets-Sheet 2
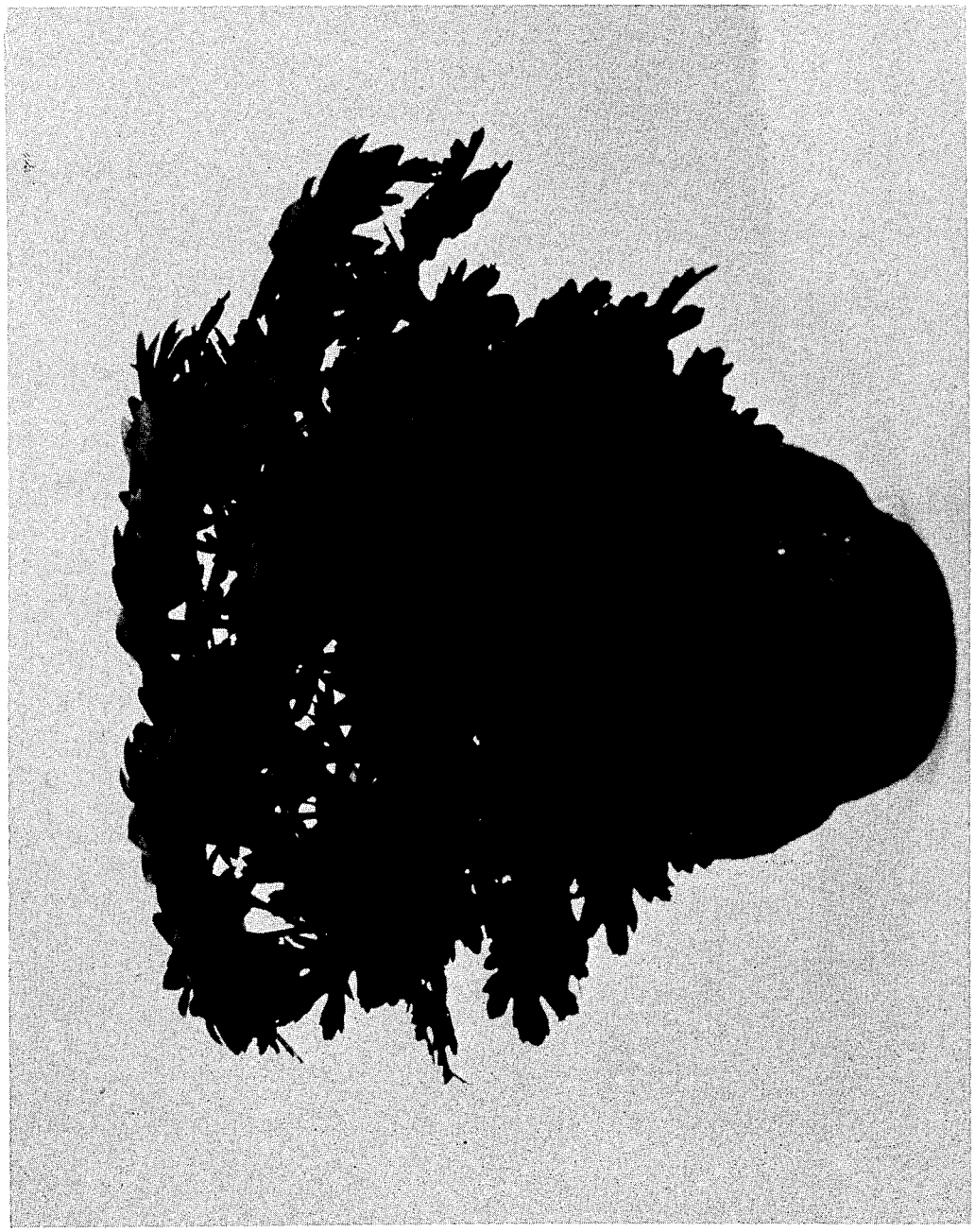

United States Patent Office

Plant Pat. 3,655

Patented Nov. 26, 1974

3,655
CHRYSANTHEMUM PLANT

Walter H. Jessel, Jr., Doylestown, and William E. Duffett, Akron, Ohio, assignors to Yoder Brothers, Inc., Barberton, Ohio

Filed Oct. 16, 1973, Ser. No. 406,797
Int. Cl. A01h *5/00*
U.S. Cl. Plt.—74 1 Claim

The present invention comprises a new and distinct cultivar of chrysanthemum plant known by the varietal name Dixie which is a seedling which is a seedling of the cultivar Dramatic × #67586–1. The cultivar Dramatic is disclosed and claimed in U.S. Plant Patent 3,189, and the other parent is identified for breeding purposes by the above breeding number.

The new cultivar is similar in many respects to the cultivar Dramatic, having the same characteristics of:

1. Bronze daisy for disbud pot usage.
2. Year round period of value as a disbud pot.
3. Requires short treatment for late winter and spring flowering.

The new cultivar is distinguished from Dramatic by the following characteristics when grown under comparable conditions:

1. Approximately ½″ larger flower size.
2. One week later response.
3. Requires short treatment for later winter and spring flowering.
4. Improved response to growth regulators.
5. Shorter and more spreading growth habit.
6. Improved form retention which provides greater bench life and home life.

7. An orange-bronze rather than a golden bronze to yellow flower color.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from January through December; coastal California, January through December; and Florida, December through April.

The accompanying photographic drawings show the unique characteristics of the new cultivar, with sheet 1 comprising a color photograph of the new cultivar as a spray pot, and sheet 2 comprising a black and white photograph showing the general growth habit and flower form of the new cultivar when grown as a disbudded pot.

In the following description, color references are made to the Munsell Color Book, 1963 edition, and comparisons are made to the cultivar Dramatic. Where only a single value or description appears for the new cultivar, the same value or description applies as well to the cultivar Dramatic.

Botanical classification: *Chrysanthemum morifolium*

| | Dixie | Dramatic |
|---|---|---|
| Bloom: | | |
| Size | 3¼″ | 2¾″. |
| Fully expanded | 3½″–4″ | 3½″. |
| Borne | Singly on disbudded branches | |
| Stems | Strong and wiry | |
| Form | Daisy (single) | |
| Permanence | 14 to 21 days | 12 to 18 days. |
| Color: | | |
| Center of flower | Yellow-green, 2.5GY5/8 to yellow, 3.75Y7/12 | Yellow-green, 5GY5/6 to yellow, 5Y8/14. |
| Base of petals | Yellow-green, 10Y7/12 | Yellow-bronze, 8.75YR7/12 to yellow, 5Y8/10. |
| Inside of petals | Bronze, 3.75YR 5/12 over amber, 2.5Y7/8 | Do. |
| Reverse of petals | Amber, 2.5Y7/8 to light yellow, 5Y8.5/8 | Yellow, 5Y8/10 to light yellow, 5Y8.5/10. |
| Tonality from a distance | Orange-bronze | Golden bronze to yellow, depending on finishing temperatures. |
| Discoloration | Bronze, 5YR5/12 over amber, 2.5Y7/8 | Yellow, 5Y8/10. |
| Petals: | | |
| Texture | Smooth | |
| Appearance and form | Open at base, deep rounded keel, tapering to a sharp tip | Open at base, flat keel, tapering to a rounded point. |
| Arrangement | Composite, whorled on a single receptacle | |
| Persistence | Resists shatter | |
| Fragrance | Typical chrysanthemum | |
| Reproductive organs: | | |
| Stamen, anthers | 200 or more | |
| Pollen | Abundant to none (functional sterility) | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Semi-spreading | Semi-upright. |
| Height | Approximately 10″–14″ when grown in a 4-cutting, 6″ pot given 9 week tall treatment from June through mid-February flowerings and 9 week short treatment from mid-February through May flowerings as defined in the timetables of Yoder Brothers, Inc., Barberton, Ohio, for the various seasons. | Approximately 14″–18″ when grown in a 4-cutting, 6″ pot given 8–9 week tall treatment as defined in the timetables of Yoder Brothers, Inc., Barberton, Ohio, for the various seasons. |
| Spread | Approximately 8″–10″ when grown in a 4-cutting, 6″ pot given 9 week tall treatment from June through mid-February flowerings and 9 week short treatment from mid-February through May flowerings as defined in the timetables of Yoder Brothers, Inc., Barberton, Ohio, for the various seasons. | Approximately 6″–8″ when grown in a 4-cutting, 6″ pot given 8–9 week tall treatment as defined in the timetables of Yoder Brothers, Inc., Barberton, Ohio, for the various seasons. |
| Foliage: | | |
| Top side | Dark green, 7.5GY3/4 | Very dark green, 10GY3/4. |
| Size | 4¾″ long, 2¾″ wide | 5½″ long, 3″ wide. |
| Quantity | Numerous | |
| Shape | Spatulate lobed | |
| Texture | Smooth | |
| Ribs and veins | Prominent | |
| Edge | Deeply indented | Moderately indented. |
| Serration | Coarse | |
| Under side | Light green, 7.5GY5/4 | Medium green, 7.5GY4/4. |
| Stipules | Prominent to occasionally rudimentary | Prominent. |

We claim:

1. A new and distinct cultivar of chrysanthemum characterized particularly as to its uniqueness when compared to the cultivar Dramatic by its approximately ½" larger flower size; one week later response; short treatment requirement for late winter and spring flowering; improved response to growth regulators; shorter and more spreading growth habit; improved form retention which provides greater bench life and home life, and by its orange-bronze rather than golden bronze to yellow flower color.

No references cited.

ROBERT E. BAGWILL, Primary Examiner

UNITED STATES PATENT OFFICE

CERTIFICATE OF CORRECTION

PATENT NO. : PP-3655

DATED : November 26, 1974

INVENTOR(S) : WALTER H. JESSEL, JR. and WILLIAM E. DUFFETT

It is certified that error appears in the above-identified patent and that said Letters Patent are hereby corrected as shown below:

In Column 1, line 19, "3. Requires short treatment for late winter and spring flowering." should be --3. Excellent high temperature tolerance.--.

Signed and sealed this 13th day of May 1975.

(SEAL)
Attest:

RUTH C. MASON
Attesting Officer

C. MARSHALL DANN
Commissioner of Patents
and Trademarks